United States Patent [19]
Westermann et al.

[11] Patent Number: 5,908,945
[45] Date of Patent: *Jun. 1, 1999

[54] ALKYLATING AGENT AND 1,4-ADDITION PROCESS OF AN ALKYL GROUP ONTO AN α,β-UNSATURATED KETONE COMPOUND

[75] Inventors: Jürgen Westermann; Klaus Nickisch, both of Berlin, Germany

[73] Assignee: Schering Aktiengesellschaft, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/530,155
[22] PCT Filed: Mar. 30, 1994
[86] PCT No.: PCT/EP94/01001
    § 371 Date: Nov. 15, 1995
    § 102(e) Date: Nov. 15, 1995
[87] PCT Pub. No.: WO94/22878
    PCT Pub. Date: Oct. 13, 1994

[30] Foreign Application Priority Data
Mar. 30, 1993 [DE] Germany .............................. 43 11 028

[51] Int. Cl.⁶ ................................. B01J 31/14; C07J 1/00
[52] U.S. Cl. ............................................. 552/634; 502/102
[58] Field of Search ..................... 552/634, 604, 552/557, 651, 643; 549/336; 568/343, 347, 312, 315; 556/182, 186, 121, 28; 502/102

[56] References Cited

U.S. PATENT DOCUMENTS

| | | | |
|---|---|---|---|
| 2,927,086 | 3/1960 | Gordon et al. | 252/429 |
| 3,065,253 | 11/1962 | Merritt et al. | 260/448.2 |
| 3,361,773 | 1/1968 | Wiechert et al. | 260/397.4 |

OTHER PUBLICATIONS

Westermann et al., "Cooper–catalyzed 1,4–additions of trialkylaluminum compounds to enones". angew. Chem. Int. Ed. Engl. vol. 32(6), pp. 1368–1370, 1993.

Ashby et al., "Transition metal catalyzed conjugate methylation of alpha, beta–unsaturated ketones by trimethylaluminum and lithium tetramethylaluminate". J. Org. Chem., vol. 39(22), pp. 3297–3299, 1974.

Alexakis et al. "Organocopper conjugate addition reaction in the presence off trimethylchlorosilane". Tetrahedron Lett. vol. 27(9), pp. 1047–1050, 1986.

Taylor et al., "Organocopper conjugate addition–enolate trapping reactions". Synthesis, pp. 364–392, 1985.

Swan et al. Organometallics in organic synthesis. pp. 51–53, 1974.

Bagnell et al. "Nickel–catalysed conjugate addition of trimethylalluminium to alpha,beta–unsaturated ketones". Aust. J. Chem., vol. 25, pp. 801–815, 1975.

Bagnell et al., Nickel–catalysed conjugate addition of trimethylaluminium to alpha, beta–unsaturated ketones. Aust. J. Chem. 28: 801–15, 1975.

Ashby and Heinsohn, Transition metal catalyzed conjugate methylation of alpha, beta–unsaturated kettones by trimethylaluminum and lithium tetramethylaluminate. J. Org. Chem. 39: 3297–3299, 1974.

Primary Examiner—José G. Dees
Assistant Examiner—Barbara Badio
Attorney, Agent, or Firm—Millen, White, Zelano, & Branigan, P.C.

[57] ABSTRACT

Disclosed is an alkylating agent that contains an aluminum reagent $Alk_{3-m}AlL_m$, in which Alk means a methyl, ethyl, n- or i-propyl, n-, i- or tert-butyl, pentyl, hexyl, heptyl or octyl group, which all can also be branched, L means an ethoxy group, a chlorine or bromine atom, and m is equal to 1 or 2, as an alkyl source or else zinc dimethyl as a methyl source, which contains in addition catalytic amounts of one or more copper(I) and/or copper(II) compounds and one (or more) silyl reagent(s) of general formula III $$R^1R^2R^3SiZ \qquad (III),$$

in which
$R^1$, $R^2$ and $R^3$ are as defined herein, as well as a process for 1,4-addition of an alkyl group to an α,β-unsaturated ketone or an α,β-double unsaturated ketone or to an α,β-unsaturated aldehyde with use of the agent according to the invention.

The alkylating agent yields biologically active compounds in excellent yields and the new alkylating agent/process is distinguished by its environmental compatibility based on a CKW (chlorinated hydrocarbon)-free reaction medium.

23 Claims, No Drawings

ALKYLATING AGENT AND 1,4-ADDITION PROCESS OF AN ALKYL GROUP ONTO AN α,β-UNSATURATED KETONE COMPOUND

This application is a 371 of PCT/EP94/01001 filed Mar. 30, 1994.

This invention relates to an alkylating agent and a process for 1,4-addition of an alkyl group to an α,β-unsaturated or an α,β-double unsaturated ketone or to an α,β-unsaturated aldehyde.

The 1-methyl introduction to steroids is a first and an important synthesis step in the production of 1-methyl steroids. Examples of this class of substances are atamestane (1) (1-methylandrosta-1,4-diene-3,17-dione), an inhibitor of estrogen biosynthesis (aromatase inhibitor), and mesterolone (2) (1α-methylandrosta-17β-ol-3-one), a steroid with an androgenic action.

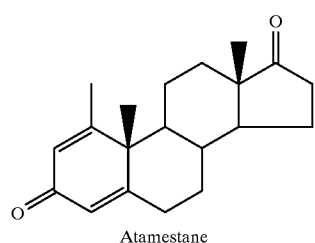

(1)

Atamestane

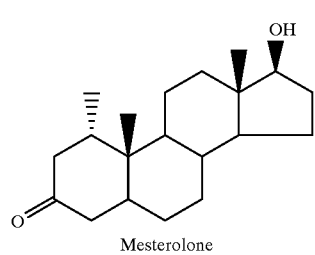

(2)

Mesterolone

A known method for 1-methyl introduction of, e.g., (3) (androsta-1,4-diene-3,17-dione) to (4) (1α-methylandrost-4-ene-3,17-dione) is the addition of dimethyl copper lithium, which is produced from methyllithium and copper(I) halides. To this end, molar amounts of the corresponding copper salt are necessary. To achieve complete conversion in the reaction to 4, a considerable excess of reagent $Me_2CuLi$ is necessary.

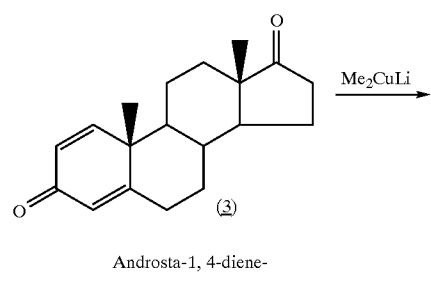

Androsta-1, 4-diene-3, 17-dione

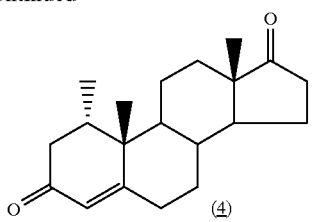

(4)

1α-Methyl-androst-4-ene-3, 17-dione

This process is the object of German Patents 2,046 640 and 2 253 087. In this case, the copper salts that accumulate in molar amounts and must be worked up constitute a serious problem, but they can be separated by filtration only with extreme difficulty.

The accumulation of sizeable amounts of copper salts can be avoided by copper(I)-catalyzed 1,4-addition with methylmagnesium halides, but in this case an undesirable 1,2-addition occurs as a secondary reaction. Thus, under these conditions, androsta-1,4-diene-3,17-dione (3) cannot be methylated to produce the desired product 1α-methyl-androst-4-ene-3,17-dione (4). Rather, by attacking at the 3-carbonyl group and after water cleavage, it forms from the intermediately formed carbinol 3-exomethylene-androsta-1,4-dien-17-one (5).

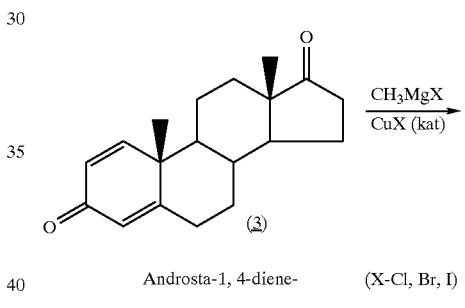

Androsta-1, 4-diene-3, 17-dione          (X-Cl, Br, I)

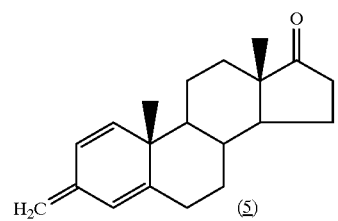

(5)

3-Exomethylene-androsta-1, 4-dien-17-one

In the literature, there are only a few examples of a 1,4-addition to an α,β-double unsaturated carbonyl system, as is the case in the example of androsta-1,4-diene-3,17-dione (3). To get directly from 3 to 4, as pointed out above, molar amounts of dimethyl copper lithium are always necessary, which must be produced from molar amounts of methyllithium and copper(I) halides.

As an additional method for introducing a methyl group into a steroid in the 1-position under catalytic conditions, the reaction sequence shown in the diagram below is described by M. Tanabe and D. F. Crowe in Can. J. Chem. 45, 475 (1967) and in German Patent 1 223 837.

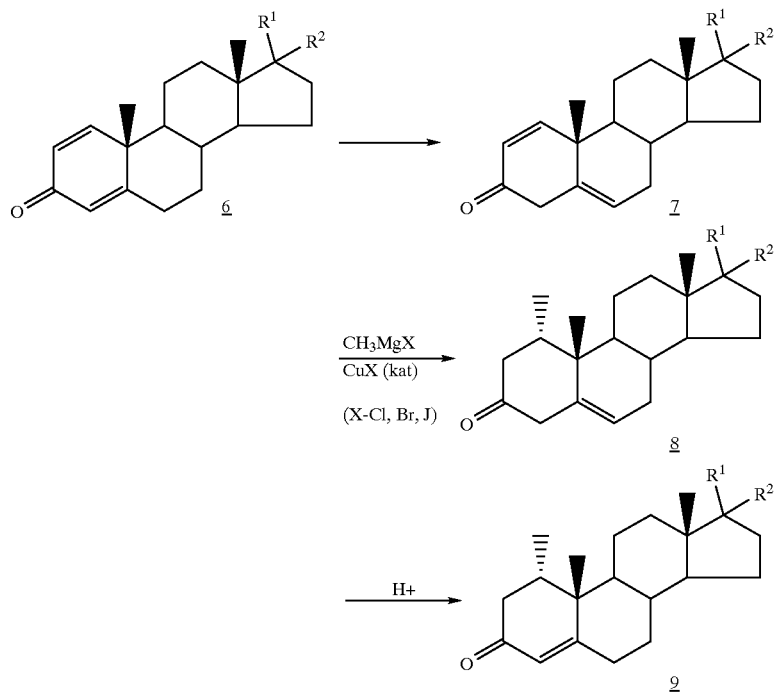

[Key:]
(kat)=(cat)
(X-Cl, Br, J)=(X-Cl, Br, I)

To this end, first conversion of 1,4-diene system 6 into a 1,5-diene steroid compound 7 is necessary.

Subsequent addition to deconjugated 1,5-diene system 7 is possible under catalytic conditions, even if in practice the yields in critical addition step 7 to 8 do not exceed 50%. Because of a larger number of stages and the associated reduced total yield, overall there is no advantageous and economical process with the above-described multistage sequence.

To date, there is no usable transition metal-catalytic process, nor suitable methylating agent for the introduction of a methyl group in the 1-position into a 3-keto-1,4-diene steroid (1,4-addition), for example, androsta-1,4-diene-3,17-dione (3).

In non-prepublished German Patent Application P 41 32 755.1 (corresponding to European Patent Application No. 92250276.0, publication number 0 534 582), a new alkylating agent, which contains trimethylaluminum or dimethyl zinc or triethylaluminum as a methyl or ethyl source as well as additional catalytic amounts of one or more copper(I) and/or copper(II) compounds, as well as a new transition metal-catalyzed process for the addition of a methyl or ethyl group to an α,β-unsaturated ketone or an α,β-double unsaturated ketone or an α,β-unsaturated aldehyde, is described using this new alkylating agent.

Preferably, the alkylating agent contains a total of 5–10 mol % of copper (I) and/or copper(II) compound relative to the α,β-unsaturated keto compound to be alkylated.

As copper(I) and/or copper(II) compound(s), in the first place, one or more compound(s) of general formula I $$CuX \text{ or } CuX_2 \tag{I}$$

in which X represents a monovalent radical and stands for chlorine, bromine, iodine, cyano, the thienyl, phenyl radical, an alkoxy, thioalkoxy radical, in which the alkyl radical contained in them has 1 to 8 carbon atoms and optionally is branched and/or unsaturated, stands for a substituted alkinyl radical R—C≡C—, in which R means a phenyl radical or an optionally branched $C_1$–$C_8$ alkyl radical, or the radical of an inorganic acid or a carboxylic acid, or stands for a two-toothed complex ligand that coordinates via oxygen and/or nitrogen atoms, except for the ligand acetylacetonate in the case of divalent copper and/or one or more compound (s) of general formula II $$Cu_2Y \text{ or } CuY \tag{II},$$

in which Y represents a divalent radical and stands for oxygen or sulfur, are suitable. If X is the radical of an inorganic acid, this is, for example, the hydrogen carbonate radical, hydrogen sulfate radical or a similar radical. As a radical of an organic acid, particularly the acetate radical is suitable.

In particular, this is copper(I) and/or copper(II) chloride or -bromide as well as copper(I) cyanide as a transition metal-catalyst.

Aluminum trimethyl and aluminum triethyl as well as zinc dimethyl can be used as a toluene or hexane solution. Because of the problems involved in the handling and the self-igniting of the metal alkyls, their use in solution is to be preferred over their use in pure form.

Aluminum-organic compounds enter into a 1,2-addition under normal reaction conditions without the addition of a catalyst to only a small extent. It is known in the literature that only under drastic reaction conditions (elevated temperatures) does such a reaction occur. Under normal conditions, such a reaction occurs only if a second molecule of trimethylaluminum is available. The first molecule of trimethylaluminum complexes the carbonyl group, to which a carbonyl group that is thus activated is added, then the second molecule [E. C. Ashby et al., J. Am. Chem. Soc., 90

(1968) 5179]. A list of aluminum alkyls is found in T. Mole and E. A. Jeffry in "Organoaluminum Compounds," Elsevier 1972, page 294 ff. 1,4-Additions are possible with Me₂AlJ, but compete with the 1,2-addition and without the addition of copper as catalyst [J. Ashley et al., J. Org. Chem., 44 (1979)] and are not selective.

In said process for 1,4-addition of a methyl or ethyl group to an α,β-unsaturated keto compound, this α,β-unsaturated keto compound is alkylated with aluminum trimethyl or zinc dimethyl or aluminum triethyl in the presence of a catalytic amount of one or more copper(I) and/or copper(II) compounds.

The desired 1,4-addition proceeds smoothly.

There are still no examples of such a catalytic procedure in the literature.

Viewed mechanically in the case of said process, a copper(I) compound is converted to a methyl-copper or dimethyl copper compound, which as such produces the 1,4-addition. After transferring a methyl group to the substrate (enone), the reactive and 1,4-selective copper reagent can be formed again from trimethylaluminum in a cyclic process.

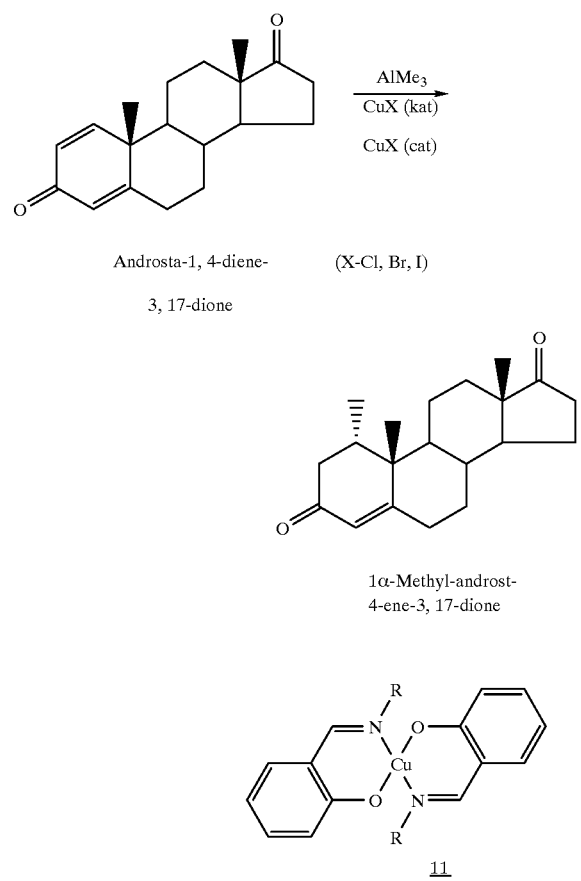

As a copper(I) halide, preferably chloride or bromide is used. The reaction is carried out preferably in tetrahydrofuran, dioxane, dimethoxyethane, toluene, or else in ethyl acetate as a solvent. In this case, surprisingly enough, no reaction with the carboxylic acid ester group of the ethyl acetate occurs under the reaction conditions found. An advantage of ethyl acetate as a solvent lies in the environmental compatibility of this solvent, which consists of the naturally occurring groups of ethyl acetate and ethanol and can be hydrolyzed or degraded in the environment in these natural molecules.

In addition to copper(I) halides, copper(II) halides, copper (II) compounds such as CuO and CuS are also suitable for the reaction.

Copper(II) complexes, in which copper is coordinated with ligands, have also turned out to be well-suited.

Such complexes of formulas 10 and 11 are described in the literature by L. Sacconi et al. in J. Chem. Soc., 1964, 276, which are derived from salicylaldehyde and can be produced from the latter.

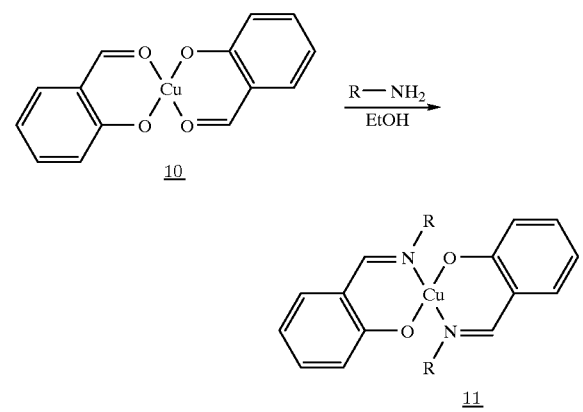

R=alkyl: methyl, ethyl, n-propyl, i-propyl, n-butyl, i-butyl, tert-butyl, or both Rs together stand for the group —(CH₂)$_n$—(n=2 or 3)

After filtration, the addition of salicylaldehyde to a copper (II) salt solution yields complex 10, which, after isolation and reaction with an amine, such as, e.g., isopropylamine, yields the Schiff base in complex 11, in which R means an isopropyl group.

Other complexes can be produced analogously.

When copper(II) compounds are used as catalysts, probably also copper(I) compounds—which are produced by reduction—represent the active species.

In all these copper(I) and copper(II) compounds, the use of catalytic portions is sufficient. In this case, an amount of 5–10 mol % of copper compound relative to the ketone used is preferably used.

In addition to the pronounced 1,4-selectivity in the addition to a 1,4-diene-3-ketosteroid, the high 1-selectivity of this addition is worth mentioning. Preferably an addition in the 1-position of the steroid to 4 takes place, which is clearly preferred over the sterically more heavily shielded 5-position.

The above-mentioned process is highly stereoselective; the proportion of the 5β-methyl compound that is formed as a by-product (in the case of methylation of (3) 5β-methyl-androst-1-ene-3,17-dione) is less than 5% of the crude product.

Another advantage of the above-described process is that acetyl protective groups remain intact under the reaction conditions. Thus, for example, the conversion of 17β-acetoxy-androst-1-en-3-one to 17β-acetoxy-1α-methyl-5α-androstan-3-one with a yield of 89% is possible.

The isolation of the products is preferably done by crystallization of the reaction products or by chromatography. The product yields can be up to 99% of theory.

The substance 1α-methylandrost-4-ene-3,17-dione (4), which is accessible according to the described catalytic process from ADD (3), is an important intermediate stage for synthesis of mesterolone (2).

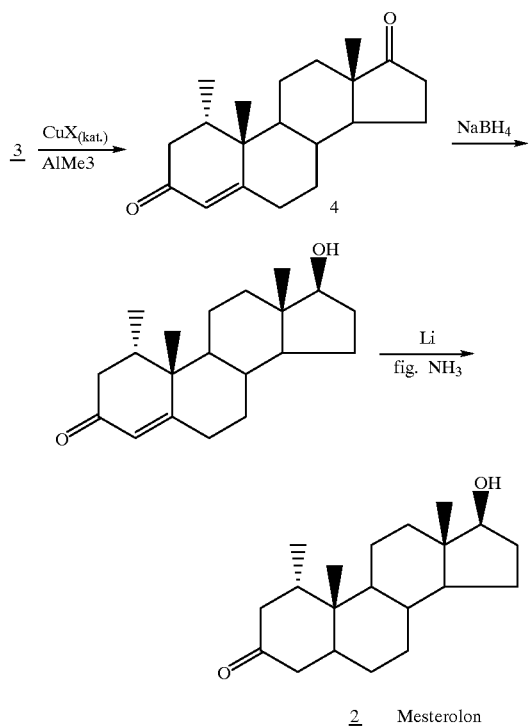

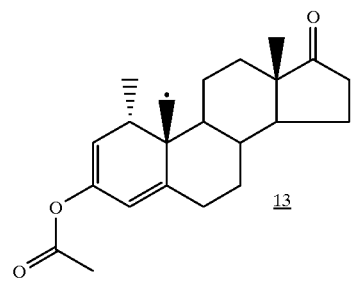

[Key:]

(kat.)=(cat.)

3-Acetoxy-1α-methyl-androsta-2,4-dien-17-one (13) is an important intermediate product for the synthesis of atamestane, which is obtained from it in high yields by stereoselective 2β-iodination, as well as subsequent hydrogen-iodide cleavage (German Patent Application P 40 15 247.2 and DE-A-37 15 869.94).

[Key:]

kat.=cat.

Mesterolon=mesterolone

Literature: DE-1 152 100 B; DE-2 046 640 B; NaBH$_4$ reduction: Fried & Edwards, Organic Reactions in Steroid Chemistry, Vol. I, 1972, p. 61 ff, Van Nostrand Reinhold Company, New York; Birch Reduction: Fried & Edwards, Vol. 1, p. 39.

Also, 17β-acetoxy-1α-methyl-5α-androstan-3-one is suitable as starting product for the production of mesterolone, which can easily be obtained from the former by saponification of the 17β-acyl group.

If a carboxylic anhydride or chloride is added to the reaction solution before the working-up of the reaction 3→4, the enolate that is present in the reaction can be trapped as an enol ester, e.g., 13.

As carboxylic anhydrides or chlorides, the anhydrides of straight-chain or branched-chain alkanecarboxylic acids with 2 to 8 carbon atoms, especially acetic acid, as well as benzoic acid, are suitable.

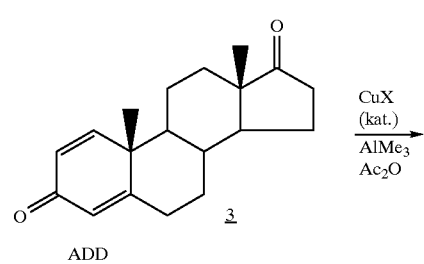

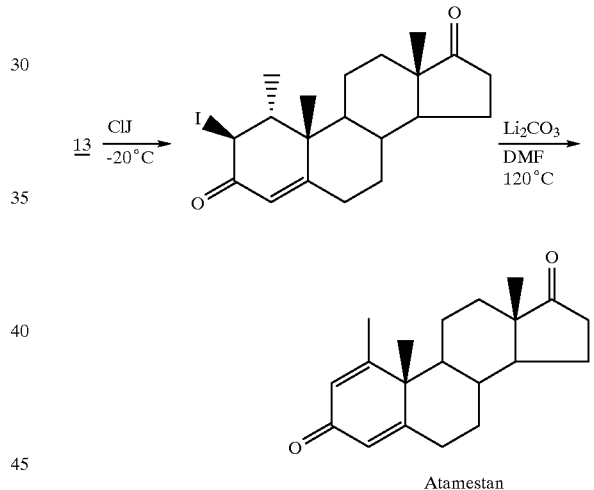

The process is also suitable for entering into a 1,4-addition to a single unsaturated carbonyl system, such as, e.g., 14.

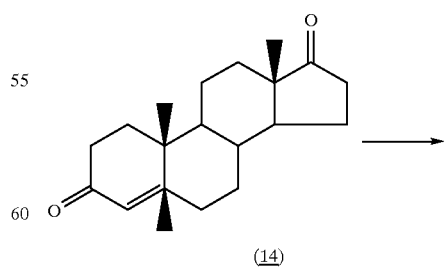

In this connection, 5β-methyl-androstane-3,17-dione (15) is produced from androst-4-ene-3,17-dione (14).

Said process can be used quite generally for 1,4-addition of a methyl or ethyl group to an α,β-unsaturated ketone in addition to the above-indicated 1,4-addition to α,β-unsaturated ketosteroids. A related example is the reaction of cyclohex-2-en-1-one (16) to 3-methylhexanone (17).

[Key:]
kat.=cat.

All reactions are preferably carried out between 0° C. and 50° C. For reaction, the ketone or ketosteroid is introduced into a suitable solvent with addition of 5–10 mol % copper catalyst under an inert-gas atmosphere, such as, e.g., nitrogen, and aluminum trimethyl (zinc dimethyl, aluminum triethyl) between 0° C. and room temperature. The reaction is hydrolyzed after about 30–120 minutes with the addition of water or a lower alcohol, and the product is then isolated.

Said agent and the above-described process are not limited to the use of trimethylaluminum or dimethyl zinc or triethylaluminum as a methyl or ethyl source. Quite analogously to what is described above, instead of the above-mentioned alkylating reagents, an aluminum reagent of formula $Alk_{3-m}AlOEt_m$, in which Alk means a methyl or ethyl group and OEt means an ethoxy group and m is equal to 1 or 2, can also be used as the reagent supplying the methyl or ethyl group within the agent or process according to the invention. If Alk stands for a methyl group, m is preferably 1 (dimethylaluminum-ethoxide).

Said agent as well as the corresponding process can be used very extensively, which is demonstrated by way of example by the production from the corresponding enones of the following compounds:

1α-Methylandrost-4-ene-3,17-dione
5β-methyl-19-norandrostane-3,17-dione
1αmethyl-17β-acetoxy-androst-4-en-3-one
5β-methylandrostane-3,17-dione
17β-hydroxy-1α-methyl-androst-4-en-3-one (1α-methyltestosterone)
17β-acetoxy-1α-methyl-5α-androstan-3-one
16α-methyl-pregna-1,4-dien-20-one
3-acetoxy-1α-methyl-androsta-2,4-dien-17-one
3-methylcyclohexanone
1α-methyl-androsta-4,6-diene-3,17-dione
3-acetoxy-16α-methyl-pregn-5-en-20-one
1α-methylandrost-4-ene-3,17-dione
1α-ethylandrosta 4,6-diene-3,17-dione
3-acetoxy-16α-ethyl-pregn-5-en-20-one
4-phenyl-pentan-2-one
4-phenyl-hexan-2-one
1α-methylandrost-4-ene-3,17-dione
2β-iodo-1α-methylandrost-4-ene-3,17-dione (→atamestane)
17β-acetoxy-2α-bromo-1α-methyl-5α-androstan-3-one
17-acetoxy-1α-ethyl-5α-androstan-3-one
1-methyl-7,7-(2,2-dimethyltrimethylenedioxy)-cis-bicyclo[3.3.0]octan-3-one
1-ethyl-7,7-(2,2-dimethyltrimethylenedioxy)-cis-bicyclo[3.3.0]octan-3-one
2-tert-butyl-5-methyl-cyclohexanone
3,3,5,5-tetramethylcyclohexanone
17β-acetoxy-1α-methyl-5α-androstan-3-one.

It has now been found that the above-described alkylating agent and the process using said agent can be further improved if to this alkylating agent there is (are) added one (or more) silyl reagent(s) of general formula III $$R^1R^2R^3SiZ \qquad (III),$$

in which
R$^1$, R$^2$ and R$^3$ can be the same or different and mean a straight-chain or branched-chain alkyl radical with 1 carbon atom, or in the branched-chain case, with 3 to 10 carbon atoms, an alkyl radical optionally substituted with 1 to 3 chlorine atoms or 1 to 3 straight-chain or branched-chain alkoxy or alkyl radicals with 1 or 3 to 6 carbon atoms, and Z means a chlorine, bromine or iodine atom, the cyano radical, a perfluoroalkylsulfonyloxy radical [$(C_nF_{2n+1}SO_2O-)$, with n=1, 2, 3 or 4], the mesylate radical $CH_3SO_2O-$, the tosyl radical p—$CH_3$—$C_6H_4$—$SO_2O-$, or another leaving group.

In addition, it has also been found that in the new alkylating agent according to this invention, not only trimethylaluminum or dimethyl zinc or triethylaluminum or a compound of formula $Alk_{3-m}AlOEt_m$, in which Alk means a methyl or ethyl group, can be used as an alkyl source, but that in general an aluminum reagent of formula $Alk_{3-m}AlL_m$, in which Alk means a methyl, ethyl, n- or i-propyl, n-, i- or tert-butyl, pentyl, hexyl, hepty or octyl group, which all can also be branched, L means an ethoxy group, a chlorine or bromine atom, and m is equal to 1 or 2, is suitable as an alkyl source in such an agent and that with such an agent, the introduction of this higher homologous alkyl radical into an α,β-unsaturated ketone or an α,β-double unsaturated ketone or into an α,β-unsaturated aldehyde is also possible.

This invention therefore relates to such an improved, silyl-containing alkylating agent as well as a process for 1,4-addition of an alkyl group Alk (Alk is a methyl, ethyl, n- or i-propyl, n-, i- or tert-butyl, pentyl, hexyl, heptyl or octyl group) utilizing the improved silyl-containing alkylating agent.

As an alkyl source, dimethyl zinc, trimethylaluminum, dimethylaluminum chloride, dimethylaluminum methoxide or triethylaluminum is preferred according to the invention.

As straight-chain or branched-chain alkyl radicals R$^1$, R$^2$, R$^3$, for example, the methyl, ethyl, propyl, butyl and tert-butyl radicals are suitable, preferably the methyl and the tert-butyl radicals.

An unsubstituted phenyl radical is preferred as an aryl radical, but also an o-, m- or p-tolyl radical or a xylyl radical is readily conceivable as a substituted aryl radical.

Of the substituents mentioned for Z, a chlorine atom or else a triflate group ($CF_3SO_2O—$) is preferred.

The silyl reagents that are preferred according to the invention are the standard silyl reagents Trimethylsilyl chloride (TMSCl)

tert-butyldimethylsilyl chloride (TBDMSCl)

tert-butyldiphenylsilyl chloride (TBDPSCl)

trimethylsilyl triflate and trimethylsilyl cyanide (TMSCN).

Especially preferred is trimethylsilyl chloride.

The new alkylating agent contains the silyl reagent of general formula III generally at a concentration of 10–1000 mol %, preferably 50–300 mol %, and especially 100–250 mol % relative to the compound to be alkylated.

The new alkylating agent is otherwise indistinguishable from said above-described alkylating agent of non-prepublished European Patent Application No. 92250276.0 (Publication No. 0534582), and the new process is quite analogous to what is described above and in the mentioned European Patent Application, but is now carried out with the use of the new alkylating agent which additionally contains a silyl reagent of general formula III.

It has been found, however, that both the non-prepublished alkylating agent and the new alkylating agent may contain even less copper(I) and/or copper(II) compound, namely a total of 0.1–10 mol % relative to the compound to be alkylated. Preferably the new alkylating agent contains a total of 1–10 mol % of Cu(I) and/or Cu(II) compound relative to the compound to be alkylated.

Through the addition of the silyl reagent of general formula III, especially trimethylsilyl chloride is used, and particularly the 1,4-addition of a methyl or ethyl group to 3-keto-$\Delta^{1,4}$ steroids is accelerated, but the new alkylating agent and its use are not limited to steroids.

In addition to accelerating the reaction, the formation of secondary products is diminished, and the proportion of starting material in the crude product is also reduced to less than 1% by the addition of one (or several different) silyl reagents of general formula III.

The yield of alkylating product can thus be significantly increased, for example, in the production of 1αMethylandrost-4-ene-3,17-dione of 77% to 89% of theory (cf. Example 1 and Example 8 as comparison examples), 1α-ethylandrost-4-ene-3,17-dione of 85% to 90% of theory (cf. Example 2 and Example 9 as comparison examples) and 2-tert-butyl-5-methylcyclohexanone of 70% to 86% of theory (cf. Example 4 and Example 10 as comparison examples).

The addition of silyl chlorides is already known in the case of other organometallic compounds (cuprates, etc.) and has been described under the following bibliographic references:

a) C. R. Johnson, T. J. Marren, *Tetrahedron Lett.*, 1987, 28, 27.

b) E. Nakamura, S. Matsuzawa, Y. Horiguchi, I. Kuwajima, *Tetrahedron Lett.*, 1986, 27, 4029.

c) C. Chuit, J. P. Foulon, J. F. Normant, *Tetrahedron*, 1980, 36, 2305; *Tetrahedron*, 1981, 37, 1385.

d) E. J. Corey, N. W. Boaz, *Tetrahedron Lett.*, 1985, 6015; ibid 1619.

e) A. Alexakis, J. Berlan, Y. Besace, *Tetrahedron Lett.*, 1986, 27, 1047.

A survey article pertaining to the addition of Lewis acids such as trimethylsilyl chloride, etc., in the case of 1,4-additions is found from Y. Yamamoto in Angew. Chem. [Applied Chemistry] 1986, 98, 945.

$BF_3$ $Et_2O$ was also studied as Lewis-acid-addition to said alkylating agent (European Patent Application No. 92250276.0). This addition does not result in any improvement of the course of reaction.

Intermediate silylenol ethers, which are hydrolyzed in the working-up, are produced in the reactions with trimethylsilyl addition. When working-up is done under mild conditions or when silyl chlorides which produce hydrolysis-stable silylenol ethers are used, these silylenol ethers can also be isolated as reaction products.

The examples below are used to provide a more detailed explanation of the invention. Examples 8, 9 and 10 are comparison examples from European Patent Application No. 92250276.0, which result in the products of Examples 1, 2 and 4 according to the invention without the addition of a silyl reagent but also produce poorer yields.

EXAMPLE 1

1α-Methylandrost-4-ene-3,17-dione 8.52 g (30 mmol) of androsta-1,4-diene-3,17-dione (1) and 86 mg (0.6 mmol) of CuBr in 70 ml of THF are dissolved under nitrogen. 28.4 ml (33 mmol) of a 10% trimethylaluminum solution in toluene is added while being cooled in an ice bath. 3.26 g (30 mmol) of trimethylsilyl chloride is added to the solution. The solution is stirred for 2 more hours at room temperature. The solution is hydrolyzed with 3 ml of water, the inorganic solid is suctioned off and rewashed. Chromatography of the crude product on silica gel with ethyl acetate/hexane yields 8 g of product 1α-methylandrost-4-ene-3,17-dione (89% of theory) of melting point 154° C.

EXAMPLE 2

1α-Ethylandrost-4-ene-3,17-dione 2.84 g (10 mmol) of androsta-1,4-diene-3,17-dione (1) and 143 mg (1 mmol) of CuBr in 15 ml of THF are dissolved under nitrogen. 5.78 ml (11 mmol) of a 1.9 molar triethylaluminum solution in toluene is added at 20° C. 2.16 g (20 mmol) of trimethylsilyl chloride is added to the solution. The solution is stirred for 3.5 more hours at room temperature. The solution is hydrolyzed with 3 ml of water, the inorganic solid is suctioned off and rewashed with ethyl acetate. Chromatography of the crude product on silica gel with ethyl acetate/hexane as eluent yields 2.8 g of 1α-ethylandrost-4-ene-3,17-dione (89% of theory) of melting point 168° C.

EXAMPLE 3

17β-Acetoxy-1α-ethylandrostan-3-one 3.31 g (10 mmol) of 17β-acetoxy-androst-1-en-3-one and 143 mg (1 mmol) of CuBr are introduced into 15 ml of dry THF. 5.79 ml (11 mmol) of a 1.9 molar solution of triethylaluminum in toluene as well as 2.16 g (20 mmol) of trimethylsilyl chloride are added at 0° C. It is stirred for 1 hour at room temperature, then hydrolyzed with 10 ml of 2N hydrochloric acid and the product is extracted with methyl tert-butyl ether. After evaporation of the solvent and recrystallization from acetone, 3.2 g of 17β-acetoxy-1α-ethylandrostan-3-one (90% of theory) of melting point 159° C. is obtained.

EXAMPLE 4

2-tert-Butyl-5-methylcyclohexanone 1.52 g (10 mmol) of pulegone (2-isopropylidene-5-methylcyclohexanone) and 14.3 mg (0.1 mmol) of CuBr in 10 ml of dry THF are introduced at room temperature. 9.5 ml (11 mmol) of 10% trimethylaluminum in toluene and 1.3 g (12 mmol) of trimethylsilyl chloride are added at 0° C. It is stirred for 5 more hours at room temperature, hydrolyzed with 5 ml of water and extracted twice with 30 ml of ether each, and the organic phases are combined. After the solvent is evaporated, the product is distilled at 10 torr and 120° C. in a bulb tube. 1.45 g (86% of theory) of 2-tert-butyl-5-methylcyclohexanone is obtained.

EXAMPLE 5

3,3-Dimethylcyclohexanone 1.1 g (10 mmol) of 3-methyl-cyclohex-2-en-1-one and 28 mg (0.2 mmol) of CuBr are introduced into 15 ml of THF. 11 ml (11 mmol) of a 10% trimethylaluminum solution in hexane and 2.16 g (20 mmol) of trimethylsilyl chloride are added at 0° C. and stirred for 3 hours at room temperature. It is hydrolyzed with 10 ml of 1N hydrochloric acid, extracted with ethyl acetate, and the solvent is evaporated. 1.21 g (97% of theory) of 3,3-dimethylcyclohexanone is obtained.

EXAMPLE 6

3-Ethyl-3-methylcyclohexanone 1.1 g (10 mmol) of 3-methyl-cyclohex-2-en-1-one and 14 mg (0.2 mmol) of CuBr are introduced into 15 ml of THF. 5.78 ml (11 mmol) of a 1.6 molar triethylaluminum solution in toluene and 2.16 g (20 mmol) of trimethylsilyl chloride are added at 0° C. and stirred for 3 hours at room temperature. It is hydrolyzed with 10 ml of 1N hydrochloric acid, extracted with ethyl acetate and the solvent is evaporated. After chromatography on silica gel, 1.26 g (90% of theory) of 3-ethyl-3-methyl-cyclohexanone is obtained.

EXAMPLE 7

1α-Methylandrost-4-ene-3,17-dione 5.68 g (20 mmol) of androsta-1,4-diene-3,17-dione (1) and 143 mg (1 mmol) of CuBr in 50 ml of THF are dissolved under nitrogen. 22 ml (22 mmol) of a solution of dimethylaluminum chloride as 10% hexane solution is added while being cooled in an ice bath. 2.6 g (24 mmol) of trimethylsilyl chloride is added to the reaction solution. The solution is stirred for 2 more hours at room temperature. For hydrolysis, the solution is mixed with 15 ml of 1 molar HCl solution and stirred for 15 more minutes. The product is extracted three times with 40 ml of ethyl acetate each. Chromatography of the crude product on silica gel with ethyl acetate/hexane as eluent yields as product 4.9 g of 1α-methylandrost-4-ene-3,17-dione (82% of theory) of melting point 152–154° C.

EXAMPLE 8

1α-Methylandrost-4-ene-3,17-dione 14.2 g (50 mmol) of androsta-1,4-diene-3,17-dione is dissolved under nitrogen atmosphere in 100 ml of anhydrous dioxane. 716 mg (5 mmol) of copper(I) bromide is added and the solution is heated to 25° C. Then, 47 ml (55 mmol) of a 10% trimethylaluminum solution in toluene is added to the reaction, so that the temperature does not rise above 35° C. Then, it is stirred for 1.5 more hours at 35° C. For hydrolysis, 2.5 ml of water mixed with 10 ml of dioxane is added to the reaction and the solution is stirred for 15 more minutes. The inorganic solid is suctioned off and rewashed with 30 ml of dioxane. After concentration by evaporation of the dioxane solution, 17 g of crude product is obtained, which is chromatographed as eluent on silica gel with hexane/ethyl acetate mixtures. After concentration by evaporation of the fractions and recrystallization from diisopropyl ether, 11.66 g of 1α-methylandrost-4-ene-3,17-dione (77% of theory) of melting point 154° C. is obtained.

EXAMPLE 9

1α-Ethylandrost-4-ene-3,17-dione 2.84 g (10 mmol) of androsta-1,4-diene-3,17-dione is dissolved under nitrogen atmosphere in 20 ml of anhydrous dioxane. 143 mg (1 mmol) of copper(I) bromide is added, and the solution is heated to 25° C. Then, 10 ml (10 mmol) of a 1 molar solution of triethylaluminum in hexane is added to the reaction, so that the temperature does not rise above 30° C. Then, it is stirred for 1.5 more hours at 30° C. For hydrolysis, 1 ml of water mixed with 5 ml of dioxane is added to the reaction, and the solution is stirred for 15 more minutes. The inorganic solid is suctioned off and rewashed with 30 ml of dioxane. After concentration by evaporation of the dioxane solution, 3 g of crude product is obtained, which is chromatographed on silica gel with a hexane/ethyl acetate mixture with an increasing portion of ethyl acetate as eluent. After concentration by evaporation of the fractions, 2.67 g of 1α-ethylandrost-4-ene-3,17-dione (85% of theory) of melting point 168° C. is obtained.

EXAMPLE 10

2-tert-Butyl-5-methyl-cyclohexanone 28.5 ml (33 mmol) of trimethylaluminum as 10% solution in toluene is instilled in 4.56 g (30 mmol) of 2-isopropylidene-5-methyl-cyclohexan-1-one (pulegone) and 214.5 mg (1.5 mmol) of CuBr in 30 ml of ethyl acetate. The reaction solution is stirred for 1 more hour at 25° C. For hydrolysis, 2 ml of water is carefully added and stirred for 15 more minutes. The inorganic solid is suctioned off, rewashed with ethyl acetate and the solution is concentrated by evaporation in a vacuum. Distillation of the crude product at 120° C./6 torr yields 3.4 g of 2-tert-butyl-5-methyl-cyclohexanone (70% of theory) as a mixture of isomers.

We claim:

1. Alkylating agent composition that comprises an aluminum reagent $Alk_{3-m} AlL_m$, in which Alk means a methyl, ethyl, n- or i-propyl, n-, i- or tert-butyl, pentyl, hexyl, heptyl or octyl group, which all can also be branched, L means an ethoxy group, a chlorine or bromine atom, and m is equal to 0, 1 or 2, as an alkyl source or else zinc dimethyl as a methyl source, characterized in that it contains in addition catalytic amounts of one or more copper(I) and/or copper(II) compounds and one (or more) silyl reagent(s) of general formula III $$R^1R^2R^3SiZ \qquad (III),$$

in which $R^1$, $R^2$ and $R^3$ can be the same or different and mean a straight-chain or branched-chain alkyl radical with 1 carbon atom, or in the branched-chain case, with 3 to 10 carbon atoms, an alkyl radical optionally substituted with 1 to 3 chlorine atoms or 1 to 3 straight-chain or branched-chain alkoxy or alkyl radicals with 1 carbon atom or, in the branched-chain case, 3 to 6 carbon atoms, and Z means a chlorine, bromine or iodine atom, the cyano radical, a perfluoroalkylsulfonyloxy radical [($C_nF_{2n+1}SO_2O$—), with n=1, 2, 3 or 4], the mesylate radical $CH_3SO_2O$—, the tosyl radical p—$CH_3$—$C_6H_4$—$SO_2O$— or another leaving group.

2. Methylating agent according to claim 1, which comprises dimethyl zinc, trimethylaluminum, dimethylaluminum chloride or dimethylaluminum ethoxide as a methyl source.

3. Ethylating agent according to claim 1, which comprises triethylaluminum as an ethyl source.

4. Alkylating agent according to claim 1, which comprises as copper(I) and/or copper(II) compound one or more compound(s) of general formula I $$CuX \text{ or } CuX_2 \qquad (I),$$

in which X represents a monovalent radical and stands for chlorine, bromine, iodine, cyano, the thienyl, phenyl radical, an alkoxy, thioalkoxy radical, in which the alkyl radical contained in them has 1 to 8 carbon atoms and optionally is branched and/or unsaturated, stands for a substituted alkinyl radical R—C≡C—, in which R means a phenyl radical or an optionally branched $C_1$–$C_8$ alkyl radical, or the radical of an inorganic acid or a carboxylic acid or stands for a two-toothed complex ligand that coordinates via oxygen and/or nitrogen atoms, except for the ligand acetylacetonate in the case of divalent copper and/or one or more compound (s) of general formula II $$Cu_2Y \text{ or } CuY \qquad (II),$$

in which Y represents a divalent radical and stands for oxygen or sulfur.

5. Alkylating agent according to claim 4, which comprises copper(I) and/or copper(II) chloride and/or -bromide and/or copper(I) cyanide.

6. Alkylating agent according to claim 1, which comprises a total of 0.1 to 10 mol % of copper(I) and/or copper(II) compound relative to the compound to be alkylated.

7. Alkylating agent according to claim 1, which comprises trimethylsilyl chloride, tert-butyldimethylsilyl chloride, tert-butyldiphenylsilyl chloride, trimethylsilyl triflate and/or trimethylsilyl cyanide as silyl reagent(s).

8. Alkylating agent according to claim 1, which comprises a total of 10 to 1000 mol % of the silyl reagent relative to the compound to be alkylated.

9. Process for 1,4-addition of an alkyl group selected from the group consisting of methyl, ethyl, -or i-propyl, n-, i- or tert-butyl, pentyl, hexyl, heptyl or octyl group, which all can also be branched to an α,β-unsaturated ketone or an α,β-double unsaturated ketone or an α,β-unsaturated aldehyde, wherein the α,β-unsaturated ketone or the α,β-double unsaturated ketone or the α,β-unsaturated aldehyde with an aluminum reagent $Alk_{3-m}AlL_m$, in which Alk means a methyl, ethyl, -or i-propyl, n-, i- or tert-butyl, pentyl, hexyl, heptyl or octyl group, which all can also be branched, L means an ethoxy group, a chlorine or bromine atom, and m is equal to 0, 1 or 2, is alkylated in the presence of a catalytic amount of one or more copper(I) and/or copper(II) compounds, together with one (or more) silyl reagent (reagents) of general formula III $$R^1R^2R^3SiZ \qquad (III),$$

in which $R^1$, $R^2$ and $R^3$ can be the same or different and mean a straight-chain or branched-chain alkyl radical with 1 carbon atom or, in the branched-chain case, with 3 to 10 carbon atoms, an alkyl radical optionally substituted with 1 to 3 chlorine atoms or 1 to 3 straight-chain or branched-chain alkoxy or alkyl radicals with 1 carbon atom or, in the branched-chain case, 3 to 6 carbon atoms, and Z means a chlorine, bromine or iodine atom, the cyano radical, a perfluoroalkylsulfonyloxy radical, the mesylate radical $CH_3SO_2O$—, the tosyl radical p—$CH_3$—$C_6H_4$—$SO_2O$— or another leaving group.

10. Process according to claim 9, wherein the unsaturated ketone or aldehyde is methylated with dimethyl zinc, trimethylaluminum, dimethylaluminum chloride or dimethylaluminum ethoxide.

11. Process according to claim 9, wherein the unsaturated ketone or aldehyde is ethylated with triethylaluminum.

12. Process according to claim 9 wherein in the presence of one or more compound(s) of general formula I $$CuX \text{ or } CuX_2 \qquad (I),$$

in which X represents a monovalent radical and stands for chlorine, bromine, iodine, cyano, the thienyl, phenyl radical, an alkoxy, thioalkoxy radical, in which the alkyl radical contained in them has 1 to 8 carbon atoms and optionally is branched and/or unsaturated, stands for a substituted alkinyl radical R—C≡C—, in which R means a phenyl radical or an optionally branched $C_1$–$C_8$ alkyl radical, or the radical of an inorganic acid or a carboxylic acid or stands for a two-toothed complex ligand that coordinates via oxygen and/or nitrogen atoms, except for the ligand acetylacetonate in the case of divalent copper and/or one or more compound (s) of general formula II $$Cu_2Y \text{ or } CuY \qquad (II),$$

in which Y represents a divalent radical and stands for oxygen or sulfur.

13. Process according to claim 12, wherein the unsaturated ketone or aldehyde is alkylated in the presence of copper(I) and/or copper(II) chloride and/or -bromide and/or copper(I) cyanide.

14. Process according to claim 9 the unsaturated ketone or aldehyde is alkylated in the presence of a total of 0.1–10 mol % of copper(I) and/or copper(II) compound relative to the α,β-unsaturated compound to be alkylated.

15. Process according to claim 9 wherein the unsaturated ketone or aldehyde is alkylated in the presence of trimethylsilyl chloride, tert-butyldimethylsilyl chloride, tert-butyldiphenylsilyl chloride, trimethylsilyl triflate and/or trimethylsilyl cyanide as silyl reagent(s).

16. Process according to claim 9 wherein the unsaturated ketone or aldehyde is alkylated in the presence of a total of 10–1000 mol % of silyl reagent relative to the compound to be alkylated.

17. Process according to claim 9 which is implemented in tetrahydrofuran, dioxane, dimethoxyethane or toluene as a solvent.

18. Process according to claim 9 which is implemented in ethyl acetate as a solvent.

19. Process according to claim 9 which is implemented at a reaction temperature of 0° C. to 50° C.

20. Process according to claim 9 wherein the α,β-unsaturated ketone is a 3-keto-1,4-diene steroid, a 3-keto-1-ene steroid, a 3-keto-4-ene steroid or a 17-acyl-16-ene steroid.

21. Process for the production of 1α-methylandrost-4-ene-3,17-dione as intermediate product for the production of 1α-methyl-17β-hydroxy-5α-androstan-3-one (mesterolone), wherein androsta-1,4-diene-3,17-dione, according to claim 9 is methylated.

22. Process for the production of a 3-acyloxy-1α-methyl-androsta-2,4-dien-17-one as intermediate product for the production of 1-methyl-androsta-1,4-diene-3,17-dione (atamestane), wherein androsta-1,4-diene-3,17-dione, according to claim 9 is methylated and the enolate that is present after the methylation in the reaction mixture is trapped with a carboxylic anhydride or -chloride of a straight-chain or branched-chain alkanecarboxylic acid with 2 to 8 carbon atoms or benzoic acid.

23. Process according to claim 22, wherein the enolate is trapped with acetic anhydride or acetyl chloride.

* * * * *